April 21, 1925. Re. 16,049

J. WERSHOW

ALCOHOL TESTER

Original Filed March 27, 1923

INVENTOR
Jacob Wershow
BY
George C. Dean
his ATTORNEY

Reissued Apr. 21, 1925. Re. 16,049

UNITED STATES PATENT OFFICE.

JACOB WERSHOW, OF NEW HAVEN, CONNECTICUT.

ALCOHOL TESTER.

Original No. 1,481,277, dated January 22, 1924, Serial No. 628,157, filed March 27, 1923. Application for reissue filed February 24, 1925. Serial No. 11,386.

*To all whom it may concern:*

Be it known that I, JACOB WERSHOW, a citizen of the United States, residing at New Haven, in the county of New Haven and State of Connecticut, have invented a new and useful Improvement in Alcohol Testers; and I do hereby declare the following, when taken in connection with the accompanying drawings and the characters of reference marked thereon, to be a full, clear, and exact description of the same, and which said drawings constitute part of this application, and represent, in—

Figure 1:
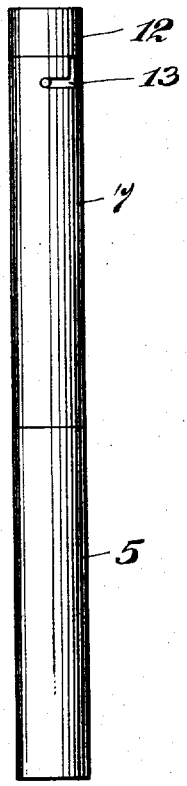

Figure 1, a side view of an alcohol tester constructed in accordance with my invention.

Figure 2:
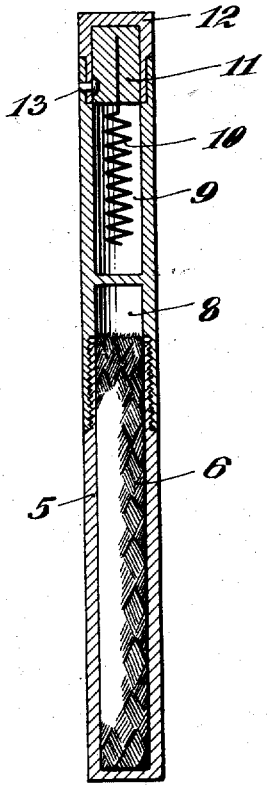

Figure 2, a vertical sectional view of the same.

This invention relates to improvement in alcohol testers, the object of the invention being to provide a device, in a compact and simple form with which any mixtures or liquid compounds can be tested to ascertain whether or not they contain wood alcohol, and the invention consists in an alcohol tester having certain details of construction as will be hereinafter described and particularly pointed out in the claims.

In carrying out my invention, I employ a wick container 5 of tubular form and adapted to contain a wick 6, the upper end of the wick container being threaded for engagement with a cap 7 which is formed in its lower end with a chamber 8 into which the upper end of the wick extends and in its upper end with a chamber 9 to house a testing element 10 which is mounted in a carrier member, such as plug 11, inserted in a head 12 movably connected with the end of the cap 7 as by a bayonet joint 13. Member 10 may be of any suitable metal or other material the surfaces of which becomes a reducing agent when sufficiently heated, copper being a well known example. By bending the metal laterally, as shown in the drawings, a large area of active reducing surface may be housed in a short space; or this member may be wire bent in the form of a coil.

This device may correspond substantially in size to a fountain pen, so as to be conveniently carried in the pocket. When a test is to be made, the parts are separated, and the wick lighted, and the testing member 10 is heated by the flame until it is in condition to act as a reducing agent, and is then plunged into the liquid to be tested and if this mixture contains wood alcohol, such wood alcohol is reduced or deoxidized sufficiently to generate and throw off formaldehyde gas in readily detectable quantities. The wick is of course saturated or impregnated with liquid or other fuel, suitable for the purpose.

I thus provide in a convenient and attractive form, an alcohol tester which is effective for the purposes desired.

I claim:

1. An alcohol tester, comprising a wick-container, a cap closing the same, and a plug carrying a coil housed within said cap.

2. An alcohol tester, comprising a wick-container, a cap threaded onto the upper end of the container and formed with upper and lower chambers, a top closing the upper chamber, a plug mounted in said cap, and a coil mounted in said plug and adapted to be housed in the upper end of the cap.

3. An alcohol tester, comprising a wick-container, a cap closing the same, and a plug carrying a laterally bent metallic tester housed within said cap.

4. An alcohol tester including a wick-container, a cap closing the same and a relatively long testing element of metal of the class adapted to serve as a reducing agent when highly heated, said testing element being removably housed within the cap.

5. An alcohol tester including a wick-container a chambered closure for the same and a relatively long testing element of metal of the class adapted to serve as a reducing agent when highly heated, said testing element being removably housed within the chamber, and laterally bent to occupy a relatively short space.

6. An alcohol tester including a wick-container, a cap closing the same and a relatively long testing element of metal of the class adapted to serve as a reducing agent when highly heated, said testing element being removably housed within the cap, said testing element being secured to a detachable closure for the cap whereby it may be housed within the cap for transportation or exposed for use.

7. An alcohol tester including a wick-container, a chambered closure for the same, a compact wire coil of metal of the class adapted to serve as a reducing agent when highly heated, means for movably supporting said wire coil within said closure so that it may be housed within the same for transportation or exposed for use.

8. An alcohol tester including a wick-container, a cap closing the same, a relatively long testing element of metal of the class adapted to serve as a reducing agent when highly heated, means supporting the testing element and constituting both a closure for the cap and a handle for the testing element.

Signed at New Haven, in the county of New Haven, and State of Connecticut, this 19th day of February, A. D. 1925.

JACOB WERSHOW.